US010813851B2

(12) United States Patent
Lee et al.

(10) Patent No.: US 10,813,851 B2
(45) Date of Patent: Oct. 27, 2020

(54) COLOR-CHANGING MICROCAPSULE COMPRISING PIGMENT CORE AND PRESSURE BREAKABLE WALL LAYER, AND PREPARATION METHOD THEREFOR

(71) Applicant: KPT LTD., Chungcheongbuk-do (KR)

(72) Inventors: Jae Uk Lee, Daejeon (KR); Byung Ho Park, Cheongju-si (KR); Ik Joo Lee, Ansan-si (KR); Yanfu Jiang, Yongin-si (KR); Woon Jang Lee, Cheongju-si (KR); Hailan Jin, Cheongju-si (KR)

(73) Assignee: KPT LTD., Chungcheongbuk-Do (KR)

( * ) Notice: Subject to any disclaimer, the term of this patent is extended or adjusted under 35 U.S.C. 154(b) by 722 days.

(21) Appl. No.: 15/519,761

(22) PCT Filed: Nov. 28, 2013

(86) PCT No.: PCT/KR2013/010908
§ 371 (c)(1),
(2) Date: Oct. 6, 2017

(87) PCT Pub. No.: WO2014/084630
PCT Pub. Date: Jun. 5, 2014

(65) Prior Publication Data
US 2018/0125765 A1 May 10, 2018

(30) Foreign Application Priority Data
Nov. 30, 2012 (KR) .................. 10-2012-0137877

(51) Int. Cl.
*A61K 8/02* (2006.01)
*C09C 1/24* (2006.01)
(Continued)

(52) U.S. Cl.
CPC .............. *A61K 8/0233* (2013.01); *A61K 8/11* (2013.01); *A61K 8/19* (2013.01); *A61K 8/29* (2013.01);
(Continued)

(58) Field of Classification Search
None
See application file for complete search history.

(56) References Cited

U.S. PATENT DOCUMENTS 4,173,492 A * 11/1979 Pollard .................... C08K 9/10
106/415
6,932,984 B1    8/2005 Babtsov et al.
(Continued)

FOREIGN PATENT DOCUMENTS

KR    1020070063908 A    6/2007
WO       2009138978 A2   11/2009

OTHER PUBLICATIONS

International Search Report and Written Opinion dated Mar. 31, 2014 for PCT/KR2013/010908.

*Primary Examiner* — Dominic Lazaro
(74) *Attorney, Agent, or Firm* — Lucas & Mercanti, LLP

(57) ABSTRACT

According to the present invention, provided is a core-shell structured chromic microcapsule having a size of 50-1,500 µm, comprising: a core comprising a colorant core (A) and an optional inner color layer (B); and a shell comprising a pressure sensitive destructible wall layer (C) encompassing the core, an optional outer color layer (D) and an optional outermost protective layer (E), wherein the colorant core allows a high content of a colorant to be contained, and the pressure sensitive destructible wall layer comprises carbon dioxide particles and a binder comprising one or more wall-forming materials and one or more lipid-base materials. The chromic microcapsule according to the present invention has high colorant content, has excellent storage dura- (Continued)

bility, maintenance durability and color-hiding property of the inner color layers, is easily destroyed by pushing, rubbing, polishing or scrubbing with the hands or a tool (cotton fabric, sponge or paper) so as to express the color of the inner color layers, and can maintain stability for a long time even if being added into a carrier.

20 Claims, 3 Drawing Sheets

(51) Int. Cl.

| | | |
|---|---|---|
| *C09C 1/36* | (2006.01) | |
| *B01J 13/04* | (2006.01) | |
| *B01J 13/22* | (2006.01) | |
| *A61Q 1/02* | (2006.01) | |
| *A61K 8/11* | (2006.01) | |
| *A61K 8/55* | (2006.01) | |
| *A61K 8/73* | (2006.01) | |
| *A61K 8/19* | (2006.01) | |
| *A61K 8/81* | (2006.01) | |
| *A61K 8/29* | (2006.01) | |
| *C09B 67/02* | (2006.01) | |
| *C09B 67/46* | (2006.01) | |
| *C09B 67/08* | (2006.01) | |
| *C09C 1/02* | (2006.01) | |

(52) U.S. Cl.
CPC .............. *A61K 8/553* (2013.01); *A61K 8/732* (2013.01); *A61K 8/8152* (2013.01); *A61Q 1/02* (2013.01); *B01J 13/04* (2013.01); *B01J 13/22* (2013.01); *C09B 67/0008* (2013.01); *C09B 67/0085* (2013.01); *C09B 67/0097* (2013.01); *C09C 1/02* (2013.01); *C09C 1/24* (2013.01); *C09C 1/36* (2013.01); *C09C 1/3676* (2013.01); *A61K 2800/412* (2013.01); *A61K 2800/42* (2013.01); *A61K 2800/43* (2013.01); *A61K 2800/621* (2013.01); *A61K 2800/622* (2013.01); *A61K 2800/624* (2013.01); *A61K 2800/651* (2013.01); *A61K 2800/652* (2013.01); *A61K 2800/654* (2013.01); *C01P 2004/84* (2013.01); *C01P 2006/10* (2013.01)

(56) References Cited

U.S. PATENT DOCUMENTS

| | | | |
|---|---|---|---|
| 2005/0129759 A1* | 6/2005 | Sojka | A61K 8/8152 424/469 |
| 2006/0093564 A1 | 5/2006 | Russ et al. | |
| 2007/0196491 A1* | 8/2007 | Venkatesh | A61K 9/2077 424/480 |
| 2008/0096979 A1* | 4/2008 | Pilgaonkar | A61K 9/282 514/783 |
| 2011/0165208 A1* | 7/2011 | Kim | A61K 8/0283 424/401 |
| 2011/0229536 A1* | 9/2011 | Kvitnitsky | A61K 8/0212 424/401 |

* cited by examiner

[Fig.1]
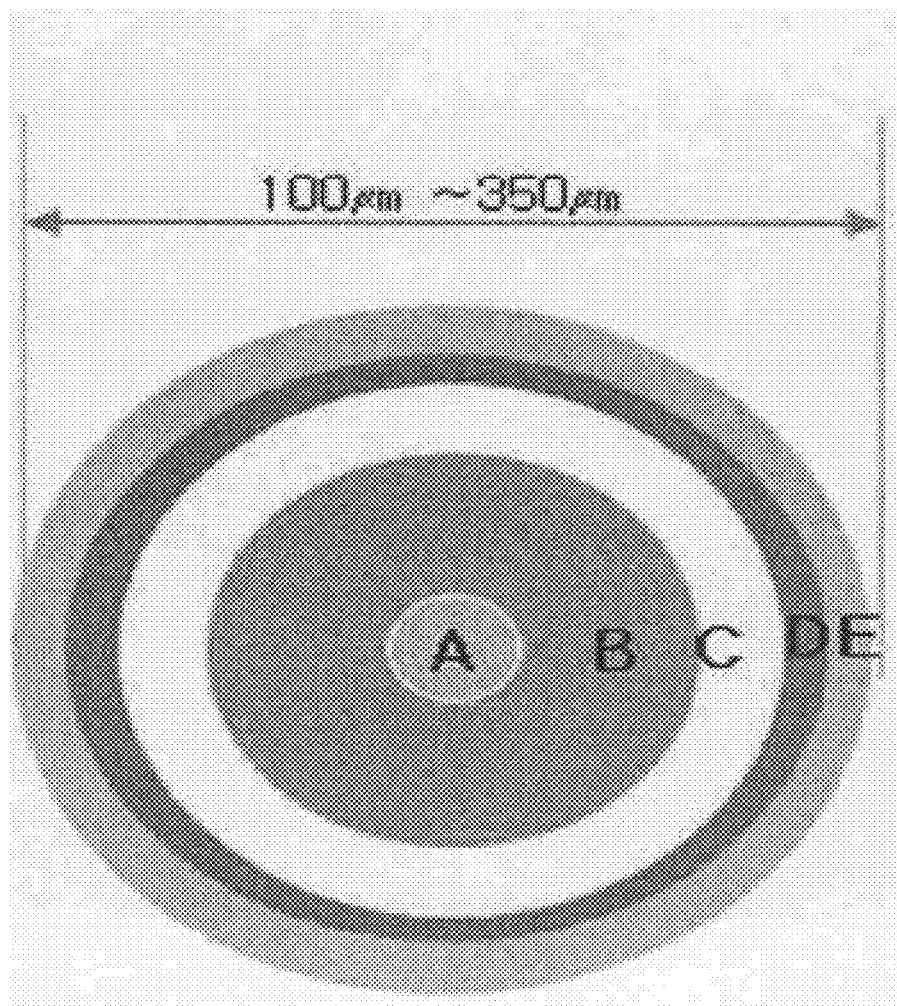

[Fig.2]
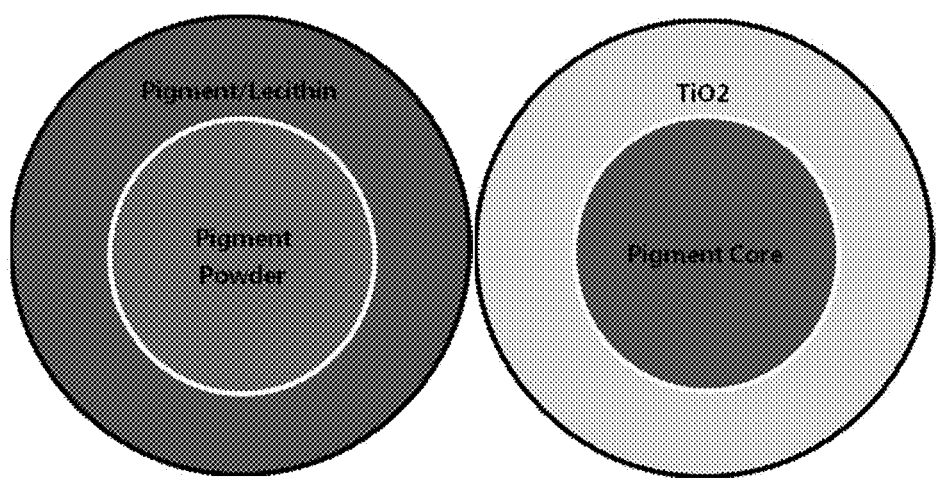
(1) Pigment Core Diagram          Magic50-BW0105-00

[Fig.3]
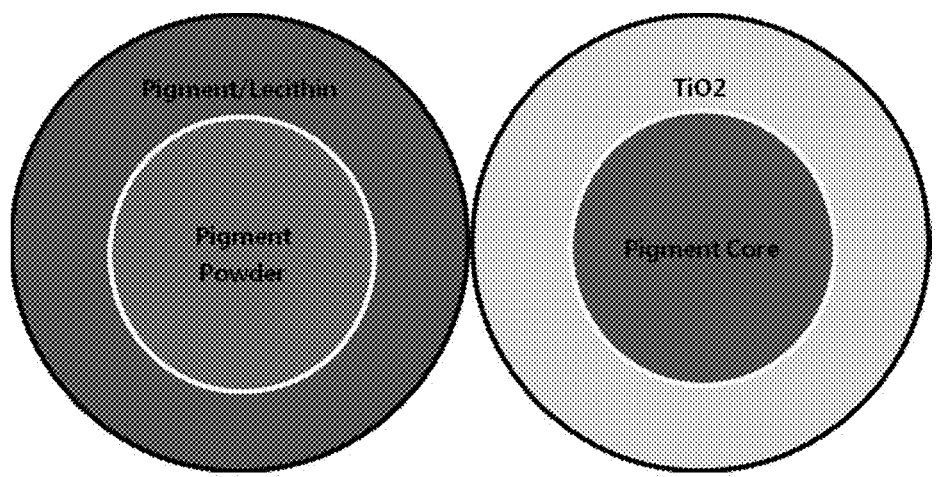
(1) Pigment Core Diagram    Magic50-BW0105-00

COLOR-CHANGING MICROCAPSULE COMPRISING PIGMENT CORE AND PRESSURE BREAKABLE WALL LAYER, AND PREPARATION METHOD THEREFOR

CROSS-REFERENCE TO RELATED APPLICATIONS

This application is a 371 of PCT/KR2013/010908, filed on Nov. 28, 2013 which claims the benefit of Korean Patent Application No. 10-2012-0137877, filed Nov. 30, 2012 the contents of each of which are incorporated herein by reference.

TECHNICAL FIELD

The present invention relates to a microcapsule with pigment core and a pressure-breakable wall layer, preparation and use thereof, more specifically, to a color-changing microcapsule with a shell structure comprising a core having at least a pigment core and an optional inner color layer, a pressure breakable-wall layer, an optional outer color layer and an optional outermost protective layer, and a method of preparing thereof.

BACKGROUND ART

The use of microencapsulation is known in various fields. Microencapsulation involves the capturing of active ingredients within a shell which can be broken or dissolved, depending on the environment in which the active ingredient is to be released. Generally, however, microencapsulation has been utilized in the pharmaceutical and quasi-pharmaceutical field, to gradually release and maintain medications, vitamins or minerals by encapsulating active ingredients within a shell which dissolves over time in the stomach.

The use of encapsulated materials to control release and improve the stability of composition is well established. The efficiency of encapsulation can be improved by reducing the relative percentage of the protective wall material and increasing the quantity of the core encapsulate. Emphasis has been place on maximizing the absolute delivery of the encapsulated core material.

Recently, color-changing microcapsules have been proposed in cosmetic field. Said color-changing microcapsules comprising a colorant, hide or do not show the colorant's color when they are not used, but will be ruptured to reveal or develop the color of the colorant when they are used or applied onto skin.

Korean Patent Laid-Open No. 10-2007-63908 discloses a friable capsule in which pigments are surrounded with a pressure-friable capsule membrane, said capsule membrane made from collagen, gelatin, agar or algin can be ruptured under pressure when used by a user to develop the pigment's color. However, said capsules have problems that they should be stored in a liquid matrix such as cosmetic carrier and the membrane is too friable under normal storage conditions as well as the colorant bleeds out through the capsule into the liquid matrix. In addition, U.S. Pat. No. 6,932,984 describes a method of preparing a microcapsule by 1) a step for dissolving or dispersing a colorant and at least one polymeric wall-forming materials selected from polyacrylate, polymethacrylate, cellulose ether, cellulose ester, polystyrene maleic anhydride copolymer in an organic solvent partially miscible with water, 2) a step for preparing an aqueous phase comprising an emulsifying agent, 3) a step for introducing the organic dispersing phase obtained in step 1) into the aqueous phase obtained in step 2) under gentle stirring to form an emulsion, 4) a step for extraction the organic solvent from the emulsion by adding an excess of water into said emulsion to obtain microcapsules, and 5) a step for separating, washing with water and drying the obtained microcapsules, or a step for introducing into about 5% alcohol solution and then separating and drying the obtained microcapsule. The present method for cosmetic raw materials containing microcapsules prepared by the patented process is now sold in the market in the trade name of Yellowcap, Redcap and Blackcap, respectively.

WO 2009/138978 discloses color-changing microcapsules containing a polymer-inorganic material shell or the polymer-plasticizer shell. The above-mentioned inorganic material is selected from among titanium dioxide, boron nitride, magnesium silicate, potassium, sodium magnesium silicate hydro alumosilicate and/or magnesium myristate and the plasticizer is selected from among tricaprylin, trilaurin, tripalmitin, triacetin, tiiethyl citrate, acetyltriethyl citrate, isopropyl myristate, or paraffin oil. However, the above-described microcapsule is prepared by an emulsion construction method and the diameter is nothing but 70 μm or less. On the other hand, EP 2 277 982A discloses a color-changing cleansing composition in 1~1000 μm size range and prepared by the fluidized bed process. The composition consists of a core (A) containing a colorant; a shell (B) containing a wall-foaming polymer, a white pigment, such as titanium dioxide, barium sulfate or zinc oxide. The shell (B) is designed to be decomposed within a specific time, for example 2-4 minutes during the hand scrubbing process, in water to release the fine colorant particles. In other words, the above mentioned shell (B) is not a pressure-breakable wall because a pressure-breakable wall should be able to decompose within a short duration during hand scrubbing, such as 1-30 seconds, to express the color.

However, with some colorant-containing microcapsules it may be difficult to permanently retain the colorant over long periods of time and when subjected to different environments and conditions. This is true for pigments, oil soluble dyes, and water soluble dyes. Thus, some microcapsules described in the prior patents and publications have been found to gradually release the colorant, or to "bleed" over a period of time, when tested for prolonged periods at elevated temperatures. Color bleed occurs when a dye or pigment, upon contacting with moisture and/or other ingredients in a formulation, migrates through or off of microspheres/microcapsules and it is more often when the shell including the pressure breakable wall surrounding the pigment is thin.

Furthermore, some pigment-containing microcapsules are too fragile and are immediately broken down at the time of application so, while there is the fun of a sudden color change, it has not been possible to realize intermediate stages in this color change or to adjust the color gradation.

PRIOR ART LITERATURE

Patent Literature (Patent Literature 1). Korean Patent Application Publication No. 10-2007-63908
(Patent Literature 2). U.S. Pat. No. 6,932,984
(Patent Literature 3). WO 2009/138978
(Patent Literature 4). EP 2 277 982 A

DESCRIPTION OF THE INVENTION

Technical Problem

One of the technical problem was to propose a stable color-changing microcapsule able to keep their properties over time, notably in term of coloring effect. Furthermore, some pigment-containing microcapsules may have some stability depending on the cosmetic composition with associated solvents/ingredients but several other pigment-containing microcapsules cannot block the internal color completely to show unattractive gray color appearance.

Another technical problem was to propose microcapsules that will not break neither during the storage by absorbing water or moisture during storage, nor during the shaking process of the composition containing the microcapsules before the use. An underlying technical problem propose the color-changing microcapsules able to survive in an extreme storage conditions (for instance, at 45° C. for 3 months).

Another technical problem was to propose a color-changing microcapsule able to break easily and homogeneously when scrubbed giving a uniform color effect without residues or unpleasant colored dots.

At last, some microcapsules may give a discomfort and/or unfavorable feeling.

Thus there is a need to provide color-changing microcapsules able to solve at least one of the above-cited problem, and notably having improved color bleed resistance. In this respect, there is a need of colorant-containing microcapsules, which capsules retain good shatter resistance and exhibit improved bleed resistance.

There is also a need to provide color-changing microcapsules which allows the desirable coloration or gradation pattern control.

There is also a need to provide color-changing microcapsules stable with a large panel of solvent/ingredient associated.

Technical Solution

The present inventors have found that a color-changing microcapsule having an inner color layer and a pressure-breakable titanium dioxide particles layer surrounding the inner color layer has a high durability during storage and handling and a high masking ability of inner color, can be easily ruptured by pressing, rubbing, wiping and/or scrubbing with hand or an implement such as cloths, sponge or paper to reveal or develop the color on the inner color layer as well as can maintain the stability for a long time when incorporated into a carrier of cosmetic, etc., thus can solve at least one problem mentioned as above.

The present inventors also have found that, by additionally coating an outer color layer and/or an outermost shell onto said color-changing microcapsules, it is possible to obtain a color-changing microcapsule having a further improved durability during storage and handling as well as a long period stability even in a carrier.

Advantageous Effects

The color-changing microcapsules according to the present invention have a high loading amount of colorant in a particle, high durability during storage and handling and a high masking ability of inner color, can be easily ruptured by pressing, rubbing, wiping and/or scrubbing with hand or an implement such as cloths, sponge or paper to reveal or develop the color on the inner color layer as well as can maintain a long period stability even in cosmetic carriers.

BRIEF DESCRIPTION OF DRAWINGS

FIG. 1 is a schematic diagram illustrating a typical structure of color-changing microcapsule of the present invention.

FIG. 2 is a schematic diagram showing the core containing pigment core, inner color layer, and pressure breakable wall structure surrounding the core.

FIG. 3 is a schematic diagram showing double layer structure of the pigment core and pressure breakable wall structure surrounding the core.

MODE OF INVENTION

The first object of the present invention is to provide a color-changing microcapsule having an average diameter of 50 to 1500 μm and a core-shell structure, wherein said core comprises a pigment core (A) and an optional inner color layer (B) The aforementioned shell comprises a pressure breakable wall layer (C), an optional outer color layer (I)) and an optional outermost protective layer (E).

Specifically, the present invention provides a color-changing capsule having an average diameter range of 50 to 1000 μm and having a core-shell structure, wherein said core comprises (A) a pigment core, and includes (C) a pressure breakable wall layer.

(A) a pigment core having an average diameter of 30 to 700 μm and comprising:
more than one colorant, and
a binder comprising at least one wall forming material and at east one lipid based material; and
(C) a pressure-breakable wall layer g a thickness of 10 to 500 μm and comprising:
titanium dioxide particles, and
a binder comprising at least one wall forming material and at least one lipid based material.

According to a preferred embodiment of the present invention, said core may comprise an inner color layer (B) as follows:

(A) a pigment core having an average diameter of 30 to 700 μm and comprising:
at least one colorant, and
a binder comprising at least one wall forming material and at least one lipid based material;
(B) any inner color layer comprising:
at least one colorant, and
a binder comprising at least one wall forming material and at east one lipid based material.

According to another preferred embodiment of the present invention, the aforementioned shell may comprise one or both of the following outer color layer (D) and outermost protective layer (E)

(D) Any outer color layer surrounding the pressure-breakable wall layer and comprising:
one or more colorant, and
a binder comprising at least one wall forming material and at least one lipid-based material; and
(E) any outermost protective layer surrounding the pressure-breakable wall layer or the outer color layer and comprising:
a shell-forming polymer selected from the group consisting of shell rock, polyacrylates, polymethacrylates, cellulose ethers, cellulose ester polystyrene-maleic anhydride copolymers and mixtures thereof.

A second object of the present invention is to provide a process for producing color-changing microcapsules comprising a pressure-breakable wall layer comprising the steps of:

(a) preparing a pigment core (A) containing a colorant and a binder, (b) optionally, coating the pigment core (A) particles with a solution in which a colorant and a binder are dispersed or dissolved to form an inner color layer (B), (c) coating the particles obtained in the step (b) with a solution in which titanium dioxide particles and a binder are dispersed or dissolved to form a pressure breakable wall layer (C), (d) optionally, coating the particles obtained in the step (c) with a solution dispersed or dissolved in the same or different colorants and binders as those used in steps (a) and (b) to form an outer color layer, and (e) optionally, coating the particles obtained in steps (c) and (d) of with a solution in which a shell-forming polymer is dispersed or dissolved to form an outermost protective layer (D), wherein the binder described above comprises a wall-forming material and a lipid-based material, wherein the wall-forming material and the lipid-based material described above are the same or different from each other.

In one preferred embodiment according to the present invention, e step (b) is included.

In one particular embodiment, the method of manufacture of the present invention comprises step (b) is included.

In another particular embodiment, the process of the present invention comprises one or both of steps (c) and (e).

Each step (a), (b), (c), (d) and (e) is carried out by a fluidized bed process or a fluidized bed coating process.

In one preferred embodiment, the solution used in this step can be water, preferably purified water, or a low boiling organic solvent such as methylene chloride, methanol or ethanol as a solvent.

In below, the present invention is explained in details with reference to drawings.

In the present invention, the color-changing microcapsule having a core comprising a colorant, and a shell comprising a pressure-breakable wall layer, at least one inner color layer, an optional outer color layer and an optional outmost layer.

FIG. 1 is a schematic diagram illustrating the structure of a color-changing microcapsule according to the present invention, wherein A represents a pigment core, B represents an inner color layer, C represents a pressure-breakable wall layer, D represents an outer color layer, and D is an outermost protective layer.

Although the color-changing microcapsule illustrated in FIG. 1 has a particle size of 100~350 μm, the color-changing microcapsule according to the present invention a particle size is generally about 50 μm or more, specifically 70 μm or more, particularly 80 μm or more, preferably 90 μm or more, more preferably 100 μm or more, and about 1500 μm or less, specifically 1200 μm or less, particularly 1000 μm or less, preferably 800 μm or less, more preferably 700 μm or less.

In addition, the color-changing microcapsule according to the present invention has a mean particle size of about 14~280 mesh (around 1400 μm~50) particularly about 24~150 mesh (around 800 μm~100 μm).

1. Pigment Core

In the present invention, the core of the microcapsules comprises a pigment core and a pigment core comprising at least one colorant and at least one binder comprising a wall-forming material and a lipid-based material. In pigment core, pigments can be understood to mean all kinds of colorants such as pigments, dyes and so on.

The pigment core may be prepared by pulverizing, pelletizing, pulverizing, granulating, encapsulating, etc. in the form of particles, powders, granules, microspheres or microcapsules, for example, one or more coloring agents, a spray drying or fluidized bed process of a solution comprising at least one wall-forming material and at least one lipid-based material.

The size of the pigment core is not particularly limited and can be suitably selected according to the final desired color-changing microcapsule. For example, the average diameter standard of the pigment core is generally about 20 μm or more, particularly 30 μm or more, specifically 40 μm or more, preferably 50 μm or more, more preferably 60 μm or more, and about 600 μm or less, specifically not more than 400 μm, preferably not more than 300 μm, and more preferably not more than 200 μm.

The radius of the pigment core is 50% or more, particularly 60% or more, specifically 70% or more, preferably 80% or more, more preferably 90% or more, based on the total radius of the microcapsule. Alternatively, the gross weight of the pigment core of the microcapsule is at least 30%, specifically 40% or less, especially 50% or less, preferably 60% or less, more preferably 70% or less, most preferably 80% or less, based on the total weight of the microcapsules. Therefore, the microcapsule of the present invention has a high loading amount of the colorant in one particle.

For pigment core, the binder may be used in an amount that colorant will not fall apart or separated from the coating layer during the coating process and/or after the removal of solvent, typically from 1 to 30% by weight, in particular from 2~25% by weight, preferably 3~20% by weight, and more preferably 5~15% by weight.

The colorant is a main component of the pigment core and can therefore be used in an amount of 70% by weight or more, particularly 75% by weight or more, preferably 80% by weight or more, more preferably 85% by weight or more, based on the total weight of the pigment core.

The pigment core may further have one or more inner color layers surrounding the pigment core. The inner color layer may comprise, for example, a first inner color layer, a second inner color layer and a third inner color layer, wherein the colorant and binder contained in each inner color layer may be the same or different from each other. In a preferred embodiment, the core may comprise one or two inner color layers, preferably one inner color layer.

When the core has a pigment core and an inner color layer, the pigment core is formed by granulation of a solution for a pigment core comprising a colorant and a binder, and the inner color layer is a solution for an inner color layer containing a colorant and a binder to coat the pigment core. The above-described coating can be carried out by a fluidized bed coating process.

The content of the inner color layer may be 20~80% by weight, specifically 30~70% by weight, and preferably 40~60% by weight based on the total amount of the core.

2. Inner Color Layer

In the present invention, the pigment core may further have one or more inner color layers and said an inner color layer can be formed by coating the pigment core with a solution having a colorant and a binder, for example, by a fluidized bed coating process.

The core can comprise one or more inner color layer including, for example, first inner color layer, second inner color layer and third inner color layer, etc., wherein the colorants and binders contained in each inner color layers are the same or different from each other. When the core comprises two or more inner color layers, a first inner color layer can be formed by coating the core-seed with a solution for first inner color layer comprising a first colorant and a first binder, a second inner color layer can be formed by coating the first inner color layer with a solution for second inner color layer comprising a second colorant and a second binder. Each coating process can be performed by a fluidized bed coating process. Each inner color layer can be circumferentially extended by centering the core-seed.

The binder can be used in an amount that colorant will not fall apart or separate from the layer during the coating process and/or after the removal of solvent, and generally can be used in an amount selected from 0.5-15% by weight, preferably 1~10% by weight, particularly 1.5~9% by weight, and more particularly 2~8% by weight in the terms of total weight of inner color layer.

The colorant is the main ingredient of inner color layer, and therefore, is used, in terms of total weight of inner color layer, in an amount of at least 40% by weight, preferably at least 75% by weight and more preferably at least 95% by weight of the inner color layer.

The inner color layer may be included in an amount of 20~80% by weight, preferably 30~70% by weight and especially 40~60% by weight, based on the total weight of the core.

3. Pressure-Breakable Wall Layer or Titanium Dioxide Particle Layer

The color-changing microcapsule of the present invention has a pressure-breakable wall layer or pressure-breakable titanium dioxide particle layer, wherein the titanium dioxide particles are discontinuously dispersed in the layer and linked to each other by a binder.

In the context of the present invention, the term "pressure-breakable" or "pressure-friable" means that a rupture can be easily made by pressing, rubbing, wiping and/or scrubbing with hand or an implement such as cloths, sponge or paper.

In the present invention, a pressure-breakable titanium dioxide particles layer can comprise particles of titanium dioxide and a binder, and said binder can comprise a wall-forming material and a lipid based material.

In the pressure-breakable wall layer of the present invention, it is believed that the titanium dioxide particles lodged in the wall-forming materials will break the pressure-breakable wall layer in an irreversible manner and facilitate or increase the disintegration or dissolution of said wall layer. Further, it is also estimated that titanium dioxide particles do a critical role for the strength, the durability, the pressure-breakability, and the after-feeling of the wall layer.

The titanium dioxide particle layer, of which thickness can vary depending on the amount of titanium dioxide used and/or the type of binder, may have a thickness of usually 10 μm or more, preferably 20 μm or more, more preferably 30 μm or more, particularly 40 μm or more, commonly 500 μm or less, preferably 400 μm or less, more preferably 300 μm or less, particularly 200 μm or less.

Alternatively, the titanium dioxide particle layer can have a content of 25~55% by weight, preferably 30~50% by weight, particularly 35~45% by weight in term of the total weight of microcapsule.

In the present invention the mean diameter or size of titanium dioxide particles is not specifically limited but has a mean diameter of usually 10 nm~20 μm, preferably 50 nm~10 μm, more preferably 100 nm~5 μm, and particularly 150 nm~5 μm. The mean diameter or size of less than 10 nm of titanium dioxide particles may result to a decrease in the pressure-breakable ability, and the mean diameter of more than 20 μm may make difficult the formation of titanium dioxide particles layer. Titanium dioxide particles having a first particle size of less than the above range but having a second particle size falling down the above particle size range can be applicable in the present invention.

The content of titanium dioxide particles in the pressure-breakable wall layer can be selected from usually 40~99% by weight, preferably 50~95% by weight, more preferably 60~90% by weight, particularly 70~95% by weight, in terms of total weight of the pressure-breakable wall layer.

4. Outer Color Layer

The color-changing microcapsule additionally comprises an optional outer color layer onto the pressure-breakable titanium dioxide particles layer. The outer color layer can be formed by coating the titanium dioxide particles layer with a solution having a colorant and a binder, for example, by the fluidized bed process.

The colorant and binder used in the outer color layer can be the same or different from those used in the inner color layer.

In general, the outer color layer is given to impart a visual color different from white color issued from the titanium dioxide particle layer and/or the color of inner color layer. Therefore, a colorant in the outer color layer can be used in an amount that does not disturb the color developed by the inner color layer when the microcapsules are applied to skins.

The content of an outer color layer can be selected, in terms of the total weight of core, from 1~60% by weight, preferably 2~50% by weight, more preferably 3~40% by weight, particularly 4~30% by weight. However, the content of a colorant in the outer color layer may be selected, in terms of total weight of colorants in the inner color layer, from 0.01~5% by weight, preferably 0.05~4.5% by weight, more preferably 0.1~4% by weight, particularly 0.5~3.5% by weight.

The content of a colorant in an outer color layer may be additionally increased if the color of the outer color layer would not disturb the color of the inner color layer. A person skilled in the art can choose the color and content of a colorant in an outer color layer in an appropriate manner by considering the color and content of colorants contained in inner color layers and the desired color to be finally developed.

5. Outermost Protective Layer

Microcapsule of the present invention can comprise a protective outermost protective layer onto a pressure-breakable wall layer or an additional outer color layer to protect the microcapsule against moisture in the air during storage or to ensure a long period stability of the microcapsule in a cosmetic carrier such as water, alcohol, etc.

The outermost protective layer can be made from at least one selected from the group consisting of shellac, polyacrylate, polymethacrylate, cellulose ether, cellulose ester and polystyrene-maleic anhydride copolymer.

The content of said outermost protective layer is selected, in terms of total weight of microcapsule, from 0.1~20.0% by weight and preferably 0.5~15% by weight. When the content of the outermost shell is less than 0.1% by weight, the shell coating may be meaningless, and when it is more than 20.0% by weight, a feeling of foreign substances may be caused.

The thickness of the outermost protective layer is usually at least 5 μm preferably 10 μm or more, more preferably 15 μm or more, especially 20 μm or more, usually at most 200 μm, preferably 150 μm or less, more preferably 120 μm or less, but it is not strictly limited.

6. Colorant or Coloring Agent

In the present invention, "colorant" include any synthetic or natural, or organic or inorganic pigments, dyes or lakes, and any colorants approved for use in cosmetics by CTFA and the FDA used in cosmetic formulations.

In the present invention, the colorant may be water-soluble or water-dispersible, or oil-soluble or oil-dispersible or with limited solubility in water.

In the present invention, thus the term "colorant" refers to organic pigments such as dyes selected from any of the well-known FD&C or D&C dyes, inorganic pigments such as metal oxides, or lakes such as the ones based on cochineal carmine, barium, strontium, calcium or aluminum and any combination (blend) thereof.

In the present invention, the following colorants can be mentioned:

carmin of cochenille;

organic pigments of azoiques, anthraquinoniques, indigoides, xantheniques, pyreniques, quinoliniques, de triphenylmethane, de fluorane colorants; and of acid colorants such as azoiques, anthraquinoniques, indigoides, xantheniques, pyreniques, quinoliniques, de triphenylmethane, de fluorane colorants, insoluble salts of sodium, potassium, calcium, baryum, aluminum, zirconium, strontium, titanium, these colorants may include at least one carboxylic or sulfonic acid group.

As to particular examples of organic pigments, those having the following trade names can be mentioned:

D&C Blue n° 4, D&C Brown n° 1, D&C Green n° 5,
D&C Green n° 6, D&C Orange n° 4, D&C Orange n° 5, D&C Orange n° 10,
D&C Orange n° 11, D&C Red n° 6, D&C Red n° 7, D&C Red n° 17, D&C Red n° 21, D&C Red n° 22, D&C Red n° 27, D&C Red n° 28, D&C Red n° 30, D&C Red n° 31, D&C Red n° 33, D&C Red n° 34, D&C Red n° 36, D&C Violet n° 2, D&C Yellow n° 7, D&C Yellow n° 8, D&C Yellow n° 10, D&C Yellow n° 11, FD&C Blue n° 1, and
FD&C Green n° 3, FD&C Red n° 40, FD&C Yellow n° 5, FD&C Yellow n° 6.

In preferred embodiments, the colorant is an inorganic pigment, more preferably a metal oxide.

Advantageously, the colorants of the multi-layer microcapsules are primary metal oxides selected from iron oxides, titanium dioxide, aluminum oxide, zirconium oxides, cobalt oxides, cerium oxides, nickel oxides, tin oxide or zinc oxide, or composite oxides, more preferably an iron oxide selected from red iron oxide, yellow iron oxide or black iron oxide, or a mixture thereof.

A person skilled in the art knows how to choose colorants and combinations of colorants to produce a desired color effect or color change.

In preferred embodiments, if white is the desired color to be developed by the color-changing microcapsule, a white colorant such as titanium dioxide can be chosen as a colorant for inner color layer. In such case, the inner color layer may be substantially the same or similar to the titanium dioxide particles layer, and thus, it can be understood that a titanium dioxide particle layer can simultaneously plays both roles of an inner color layer and pressure-breakable wall layer.

Meanwhile, a color may be achieved from one colorant alone, but most colors can be generally achieved from mixed colorants by changing the composition of colorants. Therefore, in the context of the present invention, the term "a (the) colorant" may cover both of "one colorant" and "a mixture of colorants", if there is no specific restriction.

In a preferred embodiment, the above-described core and pressure breakable wall layer may be made at least in part as metal oxides, preferably as titanium dioxide for core iron oxide and pressure breakable wall layer.

7. Binder

In general, it is difficult to form a coating layer by using only colorant component or particles without using any binder. Further, even if a coating layer without a binder is formed with difficulty, such coating layer may be easily damaged or ruptured or any components or particles may be easily removed from the coating layer. Therefore, a binder is commonly employed in order to proceed the coating process and to improve the durability of coating layer.

In the present invention, the binder comprises both of a wall-forming polymer as a wall-forming material and a lipid-base material as coating base.

In general, the coating base refers to a hydrophilic coating base, a hydrophobic coating base, or lipid-based coating base. Since the hydrophilic coating base may be extracted together with colorant into cosmetic carrier and the hydrophobic coating base may give a feeling of foreign substances due to its tow strong film property, it is preferable to employ a lipid-base coating base.

According to a particular embodiment of this invention, such lipid based material may have amphiphilic properties, that is to say having an apolar part and a polar part. Such lipid-based material can include at least one or several $C_{12}$-$C_{22}$ fatty acids chain such as selected from stearic acid, palmitic acid, oleic acid, linoleic acid, linolenic acid, etc. and mixtures thereof. Preferably these fatty acids chains are hydrogenated. Eventually, these fatty acid chains may be the apolar part of a lipid-based material. According to a particular embodiment of the invention, said lipid-based materials can be selected form the group consisting of a phospholipid such as phosphatidylcholine, phosphatidylethanolamine, phosphatidic acid or phosphatidylserine, a sphingolipid such as sphingosine-1-phosphate or sphingomyelin and ceramide, preferably ceramide or lecithin which is a phospholipid mixture, particularly hydrogenated lecithin.

One of the advantages of such lipid-based materials is that they can also act as wall-forming materials. Thus, in a particular variation of the present invention, the binder comprised with lipid-based materials alone does not depart from the scope of the present invention, with no or little use of a wall-forming polymer such as a hydrophilic polymer.

The amount of the lipid-based material to be used can be determined by considering the type and amount of other components such as coloring agent and or titanium dioxide particles as well as wall-forming materials. However, in general, the content of the lipid-based material is in the range of 0.1~30% by weight, in particular 0.2~25% by weight, preferably 0.3~20% by weight, and more preferably, may be selected from 0.4~20% by weight. If the content of the lipid base material is 0.1% by weight or more, the durability may be lowered and the durability and stability of processing and storage may deteriorate.

In the present invention, the wall-forming polymer is selected from hydrophilic polymers. The term "hydrophilic polymers" means a polymer which can form hydrogen bond with water or alcohol compounds (especially elected from lower alcohols, glycol and polyol), particularly those having O—H, N—H and S—H bonds in the molecule.

Said hydrophilic polymer can be selected from the following polymers or mixture thereof:

acrylic or methacrylic acid homopolymers or copolymers or salts and esters thereof and in particular the products sold under the names Versicol F or Versicol K by the company Allied Colloid, Ultrahold 8 by the company Ciba-Geigy, and polyacrylic acids of Synthalen K type, and salts, of polyacrylic acids, especially sodium salts (corresponding to the INCI name sodium acrylate copolymer) and more particularly a crosslinked sodium polyacrylate (corresponding to the INCI name sodium acrylate copolymer (and) caprylic/capric triglycerides) (sold under the name Luvigel EM by the company);

copolymers of acrylic acid and of acrylamide (sold in the form of the sodium salt thereof under the names Reten by the company Hercules), the sodium polymethacrylate (sold under the name Darvan No. 7 by the company Vanderbilt), and the sodium salts of polyhydroxycarboxylic acids (sold under the name Hydagen F by the company Henkel);

polyacrylic acid/alkyl acrylate copolymers, preferably modified or unmodified carboxyvinyl polymers; the copolymers most particularly preferred according to the present invention are acrylate/$C_{10}$-$C_{30}$-alkylacrylate copolymers (INCI name: Acrylates/$C_{10\text{-}30}$ Alkylacrylate Cross polymer) such as the products sold by the company Lubrizol under the tradenames Pemulen TR1, Pemulen TR2, Carbopol 1382 and Carbopol ETD2020, and even more preferentially Pemulen TR-2;

alkylacrylic/alkylmethacrylic acid copolymers and their derivatives notably their salts and their esters, such as the copolymer of ethyl acrylate, methyl methacrylate and low content of methacrylic acid ester with quaternary ammonium groups (provided under the tradename of EUDRAGIT RSPO from Evonik Degussa);

AMPS (polyacrylamidomethylpropanesulfonic acid partially neutralized with aqueous ammonia and highly cross-linked) (sold by the company Clamant);

AMPS/acrylamide copolymers such as the products Sepigel or Simulgel sold by the company SEPPIC, especially a copolymer of INCI name Polyacrylamide (and) C13-14 Isoparaffin (and) Laureth-7;

polyoxyethylenated AMPS/alkyl methacrylate copolymers (crosslinked or non-crosslinked) of the type such as Aristoflex HMS sold by the company Clamant;

anionic, cationic, amphoteric or nonionic chitin or chitosan polymers;

cellulose polymers and derivatives, preferably other than alkylcellulose, chosen from hydroxyethylcellulose, hydroxypropylcellulose, hydroxymethylcellulose, ethylhydroxyethylcellulose and carboxymethylcellulose, and also quaternized cellulose derivatives; in a preferred embodiment, the cellulose polymers is a carboxymethylcellulose;

Starch polymers and derivatives, eventually modified; in a preferred embodiment, the starch polymer is a natural starch;

vinyl polymers, for instance polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam; polyvinyl alcohol, modified polymers of natural origin, such as galactomannans and derivatives thereof, such as konjac gum, gellan gum, locust bean gum, fenugreek gum, karaya gum, gum tragacanth, gum arabic, acacia gum, guar gum, hydroxypropyl guar, hydroxypropyl guar modified with sodium methylcarboxylate groups (Jaguar XC 97-1, Rhodia), hydroxypropyltrimethylammonium guar chloride, and xanthan derivatives;

alginates and carrageenans;

glycoaminoglycans, hyaluronic acid and derivatives thereof; and mucopolysaccharides such as hyaluronic acid and chondroitin sulfates, and mixtures thereof.

Preferably, the hydrophilic polymers according to the present invention can be selected from the group consisting of polysaccharides and its derivatives, homopolymers or copolymers of acrylic or methacrylic acid or salts and esters thereof, and their mixture. Said polysaccharides and derivatives can be selected from chitosan polymers, chitin polymers, cellulose polymers, starch polymers, galactomannans, alginates, carrageenans, mucopolysaccharides, and their derivatives, and the mixture thereof.

In one preferred embodiment, the hydrophilic polymers can be selected from the group consisting of corn starch, (meth)acrylate or (alkyl)(meth)acrylate and its salts or copolymer of ester derivatives, particularly polymethyl methacrylate, cellulose or its derivatives such as carboxymethylcellulose (CMC), cellulose ester and ether and aminocellulose, and mixture thereof.

Preferred homo- and/or co-polymer of methacrylic acid and/or methacrylic acid ester are those wherein the copolymer of methyl methacrylate and ethyl acrylate has a molecule weight from 750 to 850 kDa.

The hydrophilic polymer(s) used as a wall-forming material in the present invention are not cross-linked.

The amount of polymer or wall-forming polymer used can be determined by considering the type and amount of the colorant, the titanium dioxide particles and or the lipid-based material. In general, the content of the polymer or wall-forming polymer is in the range of 0.1~30% by weight, in particular 0.2~25% by weight, preferably 0.3~20% by weight, and more preferably, may be selected from 0.4~20% by weight.

8. Color-Changing Microcapsules

The term "microcapsule", as used herein, refers to a substantially spherical microcapsule containing at least one layered coating entrapping at least one colorant and surrounding a core chemically different from the coating.

The term "multi-layer microcapsule" refers to a microcapsule consisting of an inner core surrounded by a coating based on one or more inner layer(s) and one outer layer. The one or more inner layer(s) forming the multi-layer coating of the multi-layer microcapsule and the single layer of the outer core microcapsule may be formed of the same or different wall-forming organic compound(s).

According to the present invention, the term "color-changing microcapsule" or "color-changing beads" means a microcapsule or bead wherein the color before application is different from the color after application, this difference being visible to the naked eyes. In the present invention, a pressure-friable or pressure-breakable wall layer is provided, which can be easily ruptured by pressing, rubbing, wiping and/or scrubbing with hand or an implement such as cloths, sponge or paper.

According to the present invention, at least 60%, especially at least 70%, preferably at least 80%, and more preferably at least 90% of the color changing microcapsule particles are obtained by pressing the microcapsules with a hand or tool within 1 minute, especially within 1~40 seconds, preferably within 1~30 seconds, more preferably within 1~20 seconds, of the coloring agents of the core after being polished and/or rubbed.

9. Fluidized-Bed Coating Process

In a preferred embodiment, the microcapsules can be produced by a fluidized bed process or a similar process. While the granulation by the spray drying method induces matrix particles with granular particles by particle agglomeration or randomly dispersed core material in the polymer medium, the specificity of the fluidized bed process is to concentrate one core or one or more outer layers concentrically, then it is possible to derive an actual capsule having a core shell structure enclosed therein.

Fluid bed process is disclosed by example in 'Fluid-Bed Coating, Teunou, E.; Poncelet, 2005, D. *Food Science and*

*Technology* (BocaRaton, Fla., United States), Volume 146 Issue Encapsulated and Powdered Foods, Pages 197-212.

A man skilled in the art knows how to adjust air quantity, liquid quantity and temperature allowing reproducing a microcapsule according to the invention.

Preferably a fluid bed process implemented includes Würster process and/or tangential spray process. Such process allows, contrary to pelletizing process, to conduct to spherical capsules with core surrounded by one or more circumferential layers.

In the present invention, by combining two or more compounds (ex: wall forming material and lipid-based material) in the microcapsule of different hardness and/or water solubility, it is possible to adjust the time required for colorant-encapsulated microcapsules to break down on the skin so that, by varying the method or intensity of application onto the skin, it is possible to adjust the preferred coloration or gradation pattern.

Thus, according to a preferred embodiment, the multilayers coating contains at least starch as wall forming material with at least one lipid-based material and preferably lecithin.

According to an advantageous embodiment, the microcapsules according to the invention include at least one monosaccharide or its derivatives and at least one polysaccharide or its derivatives. According to a preferred embodiment, the microcapsules include a core comprising a monosaccharide polyols preferably chosen from mannitol, erythritol, xylitol, sorbitol and a polysaccharides including ose (at least D-glucose unit).

According to a preferred embodiment, the microcapsules include three or more colorants in different layers.

According to a preferred embodiment, the microcapsules additionally includes lipid-based material chosen from phospholipids, advantageously selected from phosphoacylglycerol and in particular lecithin.

In the present invention, an organic solvent may be employed in the preparation of coating solution used in the fluidized bed coating process. The organic solvent which can be used in the present invention is not specifically restricted but preferably includes methylene chloride, methanol, ethanol, and mixture thereof. It is possible to employ any organic solvent if it can dissolve or disperse the polymers and/or lipid-based materials, has a boiling point less than that water, and has a low residual toxicity.

The present invention will be further explained by the examples, but is not restricted by them. Unless otherwise specified in the examples, % and ratio are based on weight, lecithin means hydrogenated lecithin, and the name of the substance or substance is given when the name of the contained substance or substance is clear.

Example 1

Hydrogenated lecithin (Lipoid S 100-3), and cornstarch were added to a mixed solvent of methylene chloride and ethanol (weight ratio=1:1) and completely dissolved at about 40° C. A mixed colorant of yellow iron oxide, red iron oxide and black iron oxide was added to the resulting reaction mixture and dispersed well with a homogenizer to prepare a color layer coating liquid.

The mixed colorant particles were introduced into a fluidized bed coating systemGlatt GPOG 1, bottom spray) using as a pigment core, and coated with the coloring layer coating liquid to obtain pigment core particles coated with the coloring layer.

Then, hydrogenated lecithin, PMMA (polymethylmethacrylate) and cornstarch paste were added to a mixed solvent of methylene chloride and ethanol (weight ratio=1:1) and dissolved at 40° C. to the resulting reaction mixture was added granular titanium dioxide and dispersed well with a homogenizer to prepare a titanium dioxide particle coating solution.

The pigment core particles coated with the coloring layer were coated with the resultant titanium dioxide particle coating solution to obtain color-changing microcapsule particles having a pigment core coloring layer titanium dioxide particle layer.

By using the ingredients and contents described in the below table 1, a color-changing microcapsule as shown in FIG. 2a is prepared:

Mixed Pigment (Inner color layer): Yellow:Red: Black=55.18:34.48:10.34
Layer Composition: Core (Pigment core—inner color layer)—TiO$_2$ particles layer
Size: 74~250 μm (60~200 mesh) (>99.0%)
Bulk Density: 1.23 g/ml.

TABLE 1

| Core | Pigment Core | Mixed pigment | 20.0% |
|---|---|---|---|
| | Inner Color Layer | Mixed pigment | 27.8% |
| | | Lecithin | 0.2% |
| | | Corn starch binder | 2.0% |
| Shell | TiO$_2$ Particle Layer | Titanium dioxide | 44.5% |
| | | Lecithin | 2.5% |
| | | PMMA | 1.5% |
| | | Corn starch binder | 1.0% |

Example 2

By using fluidized bed coating process described in example 1 with the ingredients and contents described in the below table 2 a color-changing microcapsule having 3 layers as shown in FIG. 2a is prepared:

Mixed Pigment (Inner color layer): Yellow:Red: Black=60.1:28.8:11.1
Layer Composition: Core (Pigment core—Inner color layer)—TiO$_2$ particles layer
Size: 74~250 μm (60~200 mesh) (>99.0%)
Bulk Density: 1.32 g/ml.

TABLE 2

| Core | (A-1) Pigment Core | Mixed pigment | 20.0% |
|---|---|---|---|
| | | Mixed pigment | 27.8% |
| | (A-2) Inner Color Layer | Lecithin | 0.2% |
| | | Corn starch binder | 2.0% |
| Shell | (B) TiO$_2$ Particle Layer | Titanium dioxide | 44.5% |
| | | Lecithin | 2.5% |
| | | PMMA | 1.5% |
| | | Corn starch binder | 1.0% |

Example 3

By using fluidized bed coating process described in example 1 with the ingredients and contents described in the below table 3 a color-changing microcapsule having 3 layers as shown in FIG. 2a is prepared:

Mixed Pigment (Inner color:Brown):(yellow(c33-9001): red(c33-8001):black(c33-7001)=49.2:39.9:10.9)
Layer Composition: Core (Pigment core—Inner color layer)—TiO$_2$ particles layer
Size: 74~250 μm (60~200 mesh) (>97.9%)
Bulk Density: 1.12 g/ml.

TABLE 3

| Core | Pigment core | Mixed pigment | 20.0% |
|---|---|---|---|
| | Inner Color Layer | Mixed pigment | 27.8% |
| | | Lecithin | 0.2% |
| | | Corn starch binder | 2.0% |
| Shell | TiO$_2$ Particle Layer | Titanium dioxide | 44.5% |
| | | Lecithin | 2.5% |
| | | PMMA | 1.5% |
| | | Corn starch binder | 1.0% |

Example 4

By using the ingredients and contents described in the below table 4, a color-changing microcapsule having 2 layers as shown in FIG. 3 is prepared:
Inner color: Brown
Size: 62~200 μm (75~250 mesh) (>99.8%)
Bulk Density: 1.33 g/ml.

TABLE 4

| Core | (A) Pigment Core | *Pigment Capsule | 57.40% |
|---|---|---|---|
| Shell | (B) TiO$_2$ Particle Layer | Titanium dioxide | 38.00% |
| | | PMMA | 2.30% |
| | | Hydrogenated Lecithin | 2.30% |

*Pigment capsule: Pigment Capsule comprises mixed Pigment 74.38%, Mannitol 22.32%, Corn Starch 2.65%, Hydrogenated Lecithin 0.65%, and the mixed Pigment comprises Yellow Iron Oxide (SunPURO ™) 49.2%, Red Iron Oxide(SunPURO ™) 39.9% and Black Iron Oxide (SunPURO ™) 10.9%.

Example 5

By using the ingredients and contents described in the below table 5, a color-changing microcapsule having 2 layers as shown in FIG. 3 is prepared:
Inner color: Brown
Mixed pigment: TiO2=50:45
Size: 62~200 μm (75~250 mesh) (>98.15%)
Bulk Density: 1.33 g/ml.

TABLE 5

| Core | (A) Pigment Core | *Pigment Capsule | 56.5% |
|---|---|---|---|
| Shell | (B) TiO$_2$ Particle Layer | Titanium dioxide | 39.15% |
| | | PMMA | 2.35% |
| | | Hydrogenated Lecithin | 2.00% |

*Pigment capsule: Pigment Capsule comprises mixed Pigment 74.31%, Mannitol 22.29%, Corn Starch 2.66%, Hydrogenated Lecithin 0.74%, and the mixed Pigment comprises Yellow Iron Oxide (SunPURO ™) 55.18%, Red Iron Oxide (SunPURO ™) 34.48% and Black Iron Oxide (SunPURO ™) 10.34%.

INDUSTRIAL APPLICABILITY

The color-changing microcapsules according to the present invention have a high loading amount of colorant in a particle, have a high durability during storage and handling and a high masking ability of inner color as well as can maintain a long period stability.

The invention claimed is:

1. A color-changing microcapsule having an average diameter of 50 to 1500 μm and having a core-shell structure, wherein the core consists of a pigment core (A) and the shell is a pressure breakable wall layer (C);
wherein the pigment core (A) has an average diameter of 30 to 800 μm and consists of:
at least one colorant, and
a binder for the core consisting of at least one wall forming material consisting of starch and at least one lipid-based material,
wherein said lipid-based material is ceramide, lecithin or hydrogenated lecithin; and
wherein the pressure breakable wall layer (C) has a thickness of 10 to 500 μm and consists of:
titanium dioxide particles, and
a binder for the wall layer consisting of at least one wall forming material and at least one lipid based material.

2. The color-changing microcapsule according to claim 1, wherein the pressure breakable wall layer (C) consists of:
5 to 99% by weight of titanium dioxide particles;
0.1 to 30% by weight of at least one wall forming material; and
0.1 to 30% by weight of at least one lipid based material.

3. The color-changing microcapsule according to claim 1, wherein the average diameter is 100 to 800 μm.

4. The color-changing microcapsule according to claim 1, wherein the wall-forming material is a hydrophilic polymer capable of forming a hydrogen bond with water or an alcohol compound.

5. The color-changing microcapsule according to claim 1, wherein the colorant is an inorganic pigment or an organic pigment.

6. The color-changing microparticle according to claim 5, wherein the colorant is at least one colorant selected from the group consisting of yellow iron oxide, red iron oxide, black iron oxide, chromium oxide green, chromium hydroxide green and ultramarine blue microcapsule.

7. The color-changing microcapsule according to claim 5, wherein the colorant is titanium dioxide.

8. A color-changing microcapsule having an average diameter of 50 to 1500 μm and having a core-shell structure,
wherein the core consists of a pigment core (A) and an inner color layer (B), and the shell is a pressure breakable wall layer (C);
wherein the pigment core (A) has an average diameter of 30 to 700 μm and consists of:
at least one colorant for the core, and
a binder for the core consisting of starch and at least one lipid-based material,
wherein said lipid-based material is ceramide, lecithin or hydrogenated lecithin;
wherein the one inner color layer (B) consists of:
at least one colorant for the inner color layer, and
a binder for the inner color layer consisting of at least one wall forming material and at least one lipid-based material; and
wherein the pressure breakable wall layer (C) has a thickness of 10 to 500 μm and consists of:
titanium dioxide particles, and
a binder for the wall layer consisting of at least one wall forming material and at least one lipid based material.

9. The color-changing microcapsule according to claim 8, wherein the colorant is an inorganic pigment or an organic pigment.

10. A color-changing microcapsule having an average diameter of 50 to 1500 μm and having a core-shell structure, wherein the core consists of a pigment core (A) and the shell is a pressure breakable wall layer (C);

wherein the shell consists of one or both of: one or more outer color layers (D), and an outermost protective layer (E);

wherein the pigment core (A) has an average diameter of 30 to 800 μm and consists of:
at least one colorant, and
a binder for the core consisting of at least one wall forming material consisting of starch and at least one lipid-based material,
wherein said lipid-based material is ceramide, lecithin or hydrogenated lecithin;

wherein the pressure breakable wall layer (C) has a thickness of 10 to 500 μn and consists of:
titanium dioxide particles, and
a binder for the wall layer consisting of at least one wall forming material and at least one lipid based material;

wherein said one or more outer color layers (D) surrounds the pressure breakable wall layer (C) and comprises:
at least one colorant for an outer color layer, and
a binder for the color layer consisting of at least one wall forming material and at least one lipid-based material; and wherein the outermost protective layer (E) surrounds the pressure breakable wall layer and consists of:
at least one shell-forming polymer selected from the group consisting of shellac, polyacrylate, polymethacrylate, cellulose ether, cellulose ester, and polystyrene maleic anhydride copolymer and mixtures thereof.

11. The color-changing microcapsule according to claim 10, wherein the colorant is an inorganic pigment or an organic pigment.

12. A method for preparing the color-changing microcapsules according to claim 1, comprising steps of:
(I) preparing the pigment core (A) containing the colorant and the binder for the core, and
(II) coating the pigment core (A) prepared in the above step (I) with a solution prepared by dispersing or dissolving titanium dioxide particles and the binder for the wall layer in a solvent, in order to form the pressure breakable wall layer (C) after removing the solvent.

13. The method according to claim 12, wherein the solvent is selected from the group consisting of methylene chloride, methanol, and ethanol.

14. The method according to claim 12, wherein coating step (II) is carried out in a fluidized bed process.

15. A method for preparing the color-changing microcapsules according to claim 8, comprising the steps of:
(I) preparing the pigment core (A) containing the colorant for the core and the binder for the core,
(II) coating the pigment core (A) prepared in step (I) with a solution prepared by dispersing or dissolving the colorant for the inner color layer and the binder for the inner color layer in a solvent, in order to form particles with an inner color layer (B) after removing the solvent, and
(III) coating the particles obtained in step (II) with a solution prepared by dispersing or dissolving titanium dioxide particles and the binder for the wall layer in a solvent, in order to form the pressure breakable wall layer (C) after removing the solvent.

16. The method according to claim 15, wherein coating steps (II) and (III) are carried out in a fluidized bed process.

17. The method according to claim 15, wherein the solvent in coating steps (II) and (III) is selected from the group consisting of methylene chloride, methanol, and ethanol.

18. A method for preparing the color-changing microcapsules according to claim 10, comprising the steps of:
(I) preparing the pigment core (A) containing the colorant for the core and the binder for the core,
(II) coating the pigment core (A) prepared in the above step (I) with a solution prepared by dispersing or dissolving titanium dioxide particles and the binder for the wall layer in a solvent, in order to form particles with pressure breakable wall layer (C) after removing the solvent,
(III) coating the particles obtained in the step (II) with a solution prepared by dispersing or dissolving the colorant for the outer color layer and the binder for the outer color layer in a solvent, in order to form particles with outer color layer (D) after removing the solvent, and
(IV) coating the particles obtained in the step (II) or (III) with a solution prepared by dispersing or dissolving the shell-forming polymer in a solvent, in order to form outermost protective layer (E) after removing the solvent.

19. The method according to claim 18, wherein coatings steps (II), (III) and (IV) are carried out in a fluidized bed process.

20. The method according to claim 18, wherein the solvent in coating steps (II), (III) and (IV) is selected from the group consisting of methylene chloride, methanol, and ethanol.

* * * * *